United States Patent
Pini et al.

(10) Patent No.: US 10,281,330 B2
(45) Date of Patent: May 7, 2019

(54) SPECTROPHOTOMETER

(71) Applicant: CONSEJO SUPERIOR DE INVESTIGACIONES CIENTIFICAS, Madrid (ES)

(72) Inventors: Valerio Pini, Madrid (ES); Priscila Monteiro Kosaka, Madrid (ES); Francisco Javier Tamayo De Miguel, Madrid (ES); Montserrat Calleja Gomez, Madrid (ES); Daniel Ramos Vega, Madrid (ES); Oscar Malvar Vidal, Madrid (ES); Jose Jaime Ruz Martinez, Madrid (ES); Mario Encinar Del Pozo, Madrid (ES)

(73) Assignee: CONSEJO SUPERIOR DE INVESTIGACIONES CIENTIFICAS, Madrid (ES)

( * ) Notice: Subject to any disclaimer, the term of this patent is extended or adjusted under 35 U.S.C. 154(b) by 0 days.

(21) Appl. No.: 15/517,809

(22) PCT Filed: Oct. 8, 2015

(86) PCT No.: PCT/ES2015/070732
§ 371 (c)(1),
(2) Date: Sep. 18, 2017

(87) PCT Pub. No.: WO2016/055683
PCT Pub. Date: Apr. 14, 2016

(65) Prior Publication Data
US 2018/0017444 A1    Jan. 18, 2018

(30) Foreign Application Priority Data
Oct. 10, 2014   (ES) .................................. 201431491

(51) Int. Cl.
G01J 3/02          (2006.01)
G01J 3/28          (2006.01)
(Continued)

(52) U.S. Cl.
CPC ............ G01J 3/2803 (2013.01); G01J 3/0208 (2013.01); G01J 3/12 (2013.01); G01J 3/28 (2013.01);
(Continued)

(58) Field of Classification Search
CPC ........ G01J 3/28; G01J 3/12; G01J 3/44; G01J 3/02; G01J 3/26; G01N 21/00; G01N 21/27
See application file for complete search history.

(56) References Cited

U.S. PATENT DOCUMENTS 5,859,700 A    1/1999   Yang
6,650,357 B1   11/2003  Richardson
(Continued)

FOREIGN PATENT DOCUMENTS

GB   2155173      9/1985
WO   2013116253   8/2013
(Continued)

OTHER PUBLICATIONS

International Application No. PCT/ES2015/070732; International Preliminary Report on Patentability (Ch1), dated Apr. 11, 2017; 5 pages.
(Continued)

*Primary Examiner* — Abdullahi Nur
(74) *Attorney, Agent, or Firm* — Dennis A. Bennett; Clifford A. Schlecht; Global Patent Group, LLC (57) ABSTRACT

The invention relates to a spectrophotometer, especially a spectrophotometer that can carry out simultaneous analysis at different points on the same sample (4), with a high spatial
(Continued)

resolution and without requiring a mechanical system for physical scanning along the sample. This is obtained by the provision of means for processing the light received by the photodetectors (5), said processing means having a correlation wherein each of the photodetectors (5) corresponds to a spatial point on the sample (4).

In the case of dark field applications, the present invention ensures the standardization of the data using the same measure.

9 Claims, 8 Drawing Sheets

(51) Int. Cl.
    *G01N 21/27*     (2006.01)
    *G01J 3/12*     (2006.01)
    *G02B 21/00*     (2006.01)
    *G01J 3/10*     (2006.01)

(52) U.S. Cl.
    CPC ............ *G01J 3/2823* (2013.01); *G01N 21/27* (2013.01); *G02B 21/00* (2013.01); *G01J 2003/104* (2013.01); *G01J 2003/106* (2013.01); *G01J 2003/282* (2013.01); *G01J 2003/2813* (2013.01); *G01J 2003/2826* (2013.01)

(56) References Cited

U.S. PATENT DOCUMENTS

| | | | |
|---|---|---|---|
| 7,391,509 B1* | 6/2008 | Deck | G02B 21/16 |
| | | | 356/301 |
| 7,443,508 B1 | 10/2008 | Vrhel | |
| 9,151,672 B2* | 10/2015 | Bolles | G01J 3/427 |
| 2004/0061784 A1* | 4/2004 | Perlin | G01N 21/55 |
| | | | 348/207.99 |
| 2008/0179526 A1 | 7/2008 | Xu | |
| 2012/0081704 A1* | 4/2012 | Morrow | G02B 6/32 |
| | | | 356/302 |
| 2012/0262563 A1 | 10/2012 | Marcelpoil | |
| 2013/0012794 A1* | 1/2013 | Zeng | A61B 1/00186 |
| | | | 600/328 |
| 2013/0130400 A1 | 5/2013 | Harbers | |
| 2014/0211199 A1* | 7/2014 | Kuo | G01J 3/44 |
| | | | 356/73 |

FOREIGN PATENT DOCUMENTS

| | | | |
|---|---|---|---|
| WO | 2016055683 A3 | 12/2015 | |
| WO | 2016055683 | 4/2016 | |

OTHER PUBLICATIONS

International Application No. PCT/ES2015/070732; International Search Report and Written Opinion of the International Searching Authority (translated and original versions), dated Dec. 2, 2015; 16 pages.

\* cited by examiner

SPECTROPHOTOMETER

CROSS REFERENCE TO RELATED APPLICATIONS

This application is a U.S. national stage filing under 35 U.S.C. § 371 of PCT International Application No. PCT/ES2015/070732, filed Oct. 8, 2015, which claims the benefit of priority to Spanish Application No. P201431491 filed Oct. 10, 2014. Each of the above-referenced applications is expressly incorporated by reference herein its entirety.

OBJECT OF THE INVENTION

The present invention relates to a spectrophotometer; specifically, the present invention relates to a spectrophotometer that can carry out simultaneous analysis at different points on the same sample, with a high spatial resolution and without requiring a mechanical system for physical scanning along the sample. This simultaneous analysis is carried out sequentially in the spectral range (for different wavelengths) to obtain a spectrometry analysis of several points on a sample and at different wavelengths.

Furthermore, the present invention makes it possible, in certain experimental conditions, to obtain normalized signals through a single measurement.

BACKGROUND OF THE INVENTION

Different types of spectrophotometers for analyzing laboratory samples that make it possible, among others, to carry out a spectral analysis of a sample with respect to a reference are known in the state of the art. The spectrophotometry process consists in using a light beam (of different wavelengths according to the analysis that is to be carried out), directing it to the sample, and analyzing the light transmitted or reflected by that sample.

In the field of standard spectrophotometry, the existing solutions are made to measure the overall optical properties of a sample, which is usually a liquid sample placed in a cuvette and measured in transmission; therefore, the spectral measurements do not have spatial resolution, as stated, for example, in document US 2013/0130400. Nevertheless, many scientific and technical applications require optical characterization of a surface with high spatial resolution, and therefore, a standard spectrophotometry system is not suitable for the entire range of applications.

In the literature there are different technical solutions for the spatially-resolved spectral analysis of a surface, also known as micro-spectrophotometric techniques. The most commonly used solution consists in coupling a spectrometer to an optical microscope by means of an optical fiber. The collimated beam of a light source is focused by means of a lens on the sample and the light that comes from a small region of the sample is analyzed by means of an optical fiber placed on the image plane of the optical microscope. Nevertheless, although this solution obtains acceptable results, it is conditioned by the diameter of the optical fiber, and furthermore, several calibrations are needed, as well as the alignment of the optical fiber, said tasks requiring a significant amount of the user's time and that said users are, or at least have access to, personnel specialized in these types of measurements.

There are other types of technical solutions that do not require an optical fiber to carry out the spectrophotometric analysis, since they already incorporate a special pierced mirror and light is transmitted through said holes instead of using the optical fiber.

These two solutions produce good spatial resolution, but they have the significant disadvantage that the spatial mapping (also called surface scanning throughout the specification) of a sample must be performed sequentially by a mechanical scanning system which always tends to be very slow. Spatial resolution in these two systems is going to be limited and established by the diameter of the fiber or mirror hole and by the accuracy of the scanning system.

Another disadvantage of these two systems is that it is always necessary to take each one of the measurements with a reference sample in order to eliminate the spectral dependency of the photodetectors, the light source and all optical components.

DESCRIPTION OF THE INVENTION

The present invention discloses a device that makes it possible to take parallel optical measurements at several points on a sample with high spatial resolution and without the need to incorporate a mechanical system for scanning on the surface.

In particular, the present invention discloses a spectrophotometer of the type that comprises a light beam emitter directed through a first optical path on a sample, and an array of photodetectors arranged on a second optical path defined as the path of the light beam after coming in contact with the sample, characterized in that it comprises means for processing the light beam received by the photodetectors, said processing means having a correlation wherein each one of the photodetectors corresponds to a spatial point on the sample.

It is important to note that the light source of the present invention has means for modifying the wavelength of the light generated, such that it has means for sequentially modifying the spectral component of the generated light and, consequently, the spectral component for which the sample analysis will be carried out.

By way of example, the following options for light emitters are envisaged:

1) Light source with a broad spectral band (such as a white light-emitting bulb) with a length selector (such as a monochromator, optical filters, prisms, etc.); or
2) A series of multiple light sources at a single wavelength (for example, multiple LEDs or multiple LASERs), such that a wavelength selector would not be needed; they would only need to have means for selecting the LED that illuminates the sample, such that wavelength scanning can be performed by changing from one LED to another.

In an especially preferred embodiment, the source of the light beam comprises a monochromator to selectively control the wavelength sent to the sample, such that a light beam of a certain wavelength is emitted. Therefore, a simultaneous analysis at different points on the same sample at the same wavelength is carried out and, afterwards, another wavelength is selected with the monochromator, such that the sample is sequentially illuminated with several wavelengths.

The spectrophotometer of the present invention can be made for bright field and dark field applications, both for measurements of reflection or transmission, provided that optical components suitable for each of the techniques are used.

Additionally, the spectrophotometer of the present invention can be made to take measurements of crossed polarization, provided that the appropriate polarizers are coupled along the beam that hits the sample and along the path of the beam that points towards the array of photodetectors.

Preferably, the array of photodetectors is a CCD camera in which a series of pixels thereof comprises a photodetector. Said series can be one pixel or an array of them.

For applications of microspectrophotometry, the spectrophotometer of the present invention has an array of lenses on the first path that serve to collimate and focus the light so that readings can be made even in applications that require a submicrometric analysis.

In particular embodiments of the present invention, the source of the light beam comprises a monochromator, such that a light beam of a certain wavelength is emitted. In this way, a parallel analysis at different points on the same sample at the same wavelength is carried out.

Among the different beam sources with a broad spectral band that can be used to carry out the spectrophotometric analysis, the beam source can be a visible, ultraviolet and/or infrared light source.

Regarding the transmission means of the optical signals, the present invention envisages that the second path of the light beam does not comprise wired transmission means of light. In this way, the resolution of the device is not dependent on the caliber of, for example, an optical fiber.

In a first exemplary embodiment of the present invention, the second path is the path defined by the light when reflected by the sample.

In another embodiment of the present invention, the second path is the path defined by the light when it passes through the sample.

DESCRIPTION OF THE DRAWINGS

As a complement to the description provided herein and for the purpose of helping to make the characteristics of the invention more readily understandable, in accordance with a preferred practical embodiment thereof, said description is accompanied by a set of drawings constituting an integral part of the same, which by way of illustration and not limitation represent the following.

PREFERRED EMBODIMENT OF THE INVENTION

Figure 1:
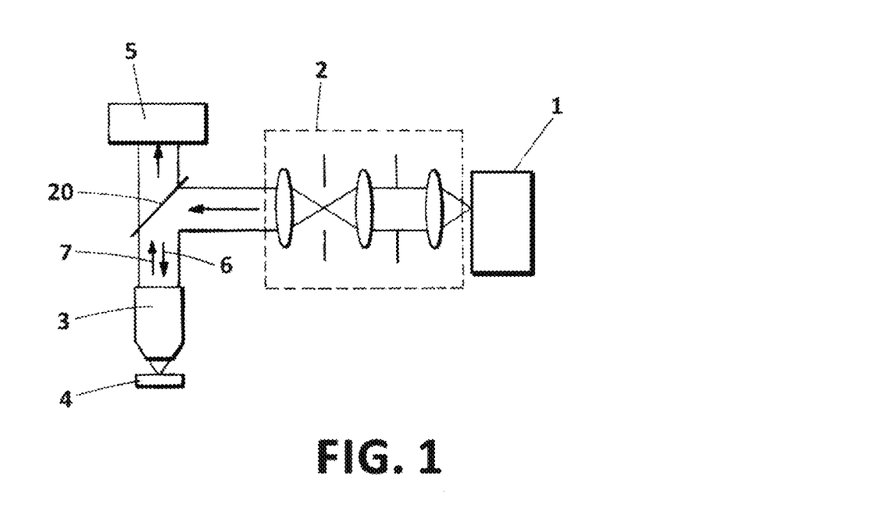
FIG. 1 shows a schematic view of an embodiment of the present invention wherein the measurement is made by using the light reflected by the sample.

FIG. 1 shows a first embodiment by way of example of the first invention; in particular, FIG. 1 shows a light emitter array (1) and transmission and/or adaptation means of said light (2) and, in this particular case, there is a beam splitter (20) and a microscope objective (3) focused on the sample (4).

The outlet of said light emitter array (1) is a light beam that subsequently passes towards the transmission and/or adaptation means of said light (2), it being possible for said transmission and/or adaptation means of light (2) to comprise lenses and collimators, among others. The outlet of these light transmission and/or adaptation means (2) has the incident beam (6) that is sent to the sample (4) and, optionally, there can be intermediate elements such as beam splitters (20), lenses (such as microscope objectives (3)), etc. This entire path is defined as a first path and, hereinafter, this beam that is applied to the sample will be referred to as the incident beam (6). Afterwards, the light reflected is analyzed, this light being the new beam that, subsequently, is referred to as the resulting beam (7).

The resulting beam (7) once again passes through the microscope objective (3) and the beam splitter (20) directs this resulting beam (7) to the array of photodetectors (5).

In this particular case, a microscope objective (3) is used to be able to analyze the sample with a higher resolution, however, this microscope objective (3) should be understood as a merely optional element, since it can be omitted if there are very high resolution means for analyzing the resulting beam or if the photodetectors themselves have enough spatial resolution to carry out the analysis without needing to incorporate said objective.

Figure 2:
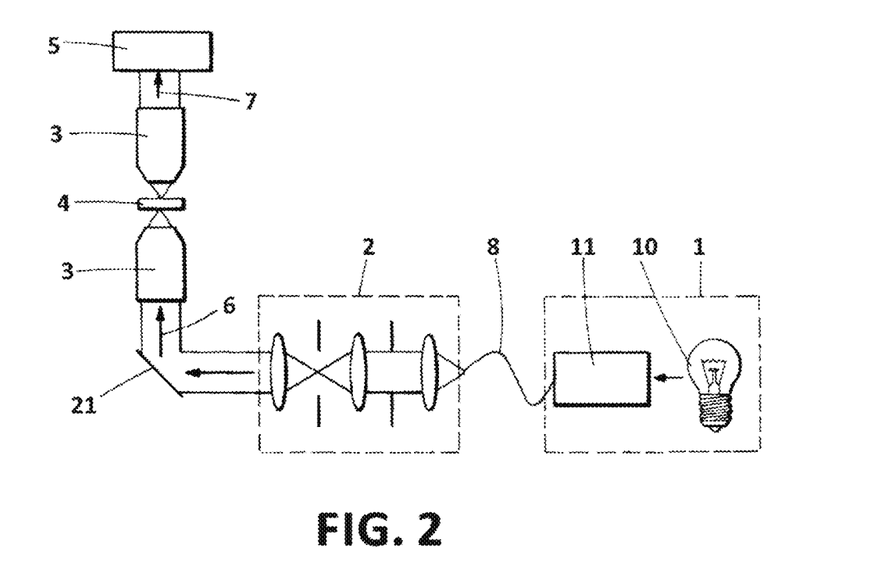
FIG. 2 shows a schematic view of a second embodiment of the present invention wherein the measurement is made by using the light transmitted by the sample.

Another possible embodiment of the present invention is described below in reference to FIG. 2. This configuration is useful for the spectral characterization of samples in transmission due to the fact that the incident beam and the resulting beam do not share any optical element. In this embodiment, independent microscope lenses (3) are used, one for the incident beam (6) and another for the resulting beam (7).

In this embodiment, a light source (10) with a very broad spectral band (for example, a halogen lamp, a mercury lamp, a xenon lamp) connected to a wavelength selector (which can be a monochromator (11), a prism, a series of optical filters, etc.) is shown. This configuration makes it possible to sequentially send predetermined wavelengths. The sequential and selective change of the wavelength can be carried out, for example, by motorizing the wavelength selector.

In this embodiment, the sample analysis can alternatively be carried out through the use of an array of light emitters at different wavelengths which can be turned on sequentially.

At the outlet of said light emitting array (1), the light can be transferred, for example, by an optical fiber (8) (or any other type of optical guide) to the transmission and/or adaptation means of said light (2), which can comprise lenses or collimators, among others. The outlet of these transmission and/or adaptation means of the light (2) has the incident beam (6) that is sent to the sample (4) and there can be intermediate elements such as mirrors (21), microscope lenses (3), etc.

Unlike the case in FIG. 1, in this exemplary embodiment the light that passes through the sample (4) is analyzed for which we could have microscope lenses (3) for the light that passes through the sample and we could likewise analyze the resulting beam (7) through an array of photodetectors (5).

It is important to note that the present invention lacks wired transmission means of light along the resulting beam (7). Nevertheless, in some embodiments wired means can be used to transmit the incident light beam or light beams at any point between the light source and the sample.

This lack of wired transmission means of light (or optical fibers) of the resulting light (7) has the advantage that the spatial resolution of an analyzed sample does not depend on the diameter of the optical fiber.

To illustrate this effect, it is enough to assume that it aims to analyze a sample to determine artifacts on said sample with a diameter of 5 µm on a sample of 1 mm2. To be able to detect these artifacts through standard spectrophotometric techniques, there must be an optical fiber with a diameter smaller than the artifacts (at least 1 µm), scan the entire sample, carry out tasks to align it and process data to determine what part of the sample is being analyzed. Nevertheless, the ability to make spectral measurements in parallel and simultaneously on the entire sample makes it possible to find a small artifact on a relatively large sample. For example, with an incident beam (6) that has a diameter of at least 1 mm2 and an array of photodetectors (5) with a resolution that makes it possible to detect said artifacts and, most of all, it is not necessary to have a system for physical scanning along the sample. Alternatively, there can be microscope lenses (3) that magnify the resulting beam (7), facilitating the work of the array of photodetectors (5) since the image of the sample is magnified by said lenses.

Figure 3:
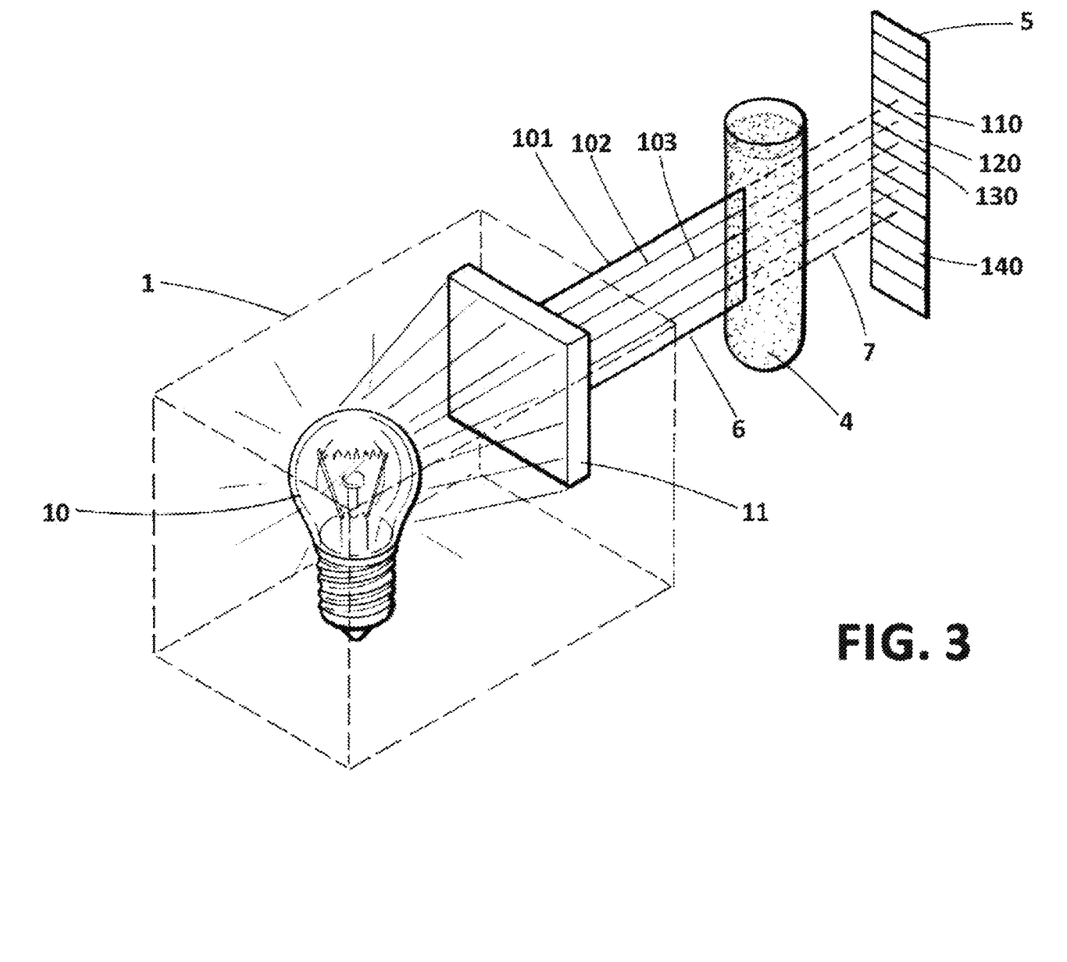
FIG. 3 shows a perspective view of the basic elements of a spectrophotometer according to the present invention.

FIG. 3 is a perspective view of an exemplary embodiment of the present invention.

This figure shows a light emitter array (1) that comprises a light source (10) and a monochromator (11) (or, more generally, a wavelength selector). To facilitate understanding of the present invention, it is assumed that the beam at the outlet of the monochromator (11) (in other words, the incident beam (6)) is a linear beam. Furthermore, in particular embodiments of the present invention, the beam can also be a two-dimensional beam, the wavelength of which can be modified sequentially.

The resulting beam is analyzed such that a first component (101) corresponds to a certain point on the sample and this point on the sample is assigned a first photodetector (110). Likewise, a second component (102) corresponds to a second point on the sample assigned to a second photodetector (120), and a third component (103) corresponds to a third photodetector (130). All points on the analyzed sample will be sequentially illuminated on the different pre-selected wavelengths and similarly analyzed for each of those wavelengths. This correlation is stored in processing means, such as a computer, and can be configured according to the sample. Furthermore, in said processing means, the size of the sample can be analyzed, for example, by means of a fourth photodetector (140) which does not receive light, and therefore, the limits of the container of the sample can be defined which would be useful for later processes.

Indeed, it is enough to have a correlation between points on the sample and the photodetectors, such that it can be determined that the analysis carried out by each of the detectors corresponds to determined spatial coordinates on the sample.

Although FIG. 3 relates to a linear incident beam in order to easily explain the invention, it is important to reiterate that, for example, circular beams with a diameter greater than that of the sample can be used and that the array of photodetectors (5) is not a row of photodetectors, but rather a matrix of them, for example, as an array of photodetectors (5) that can have a CCD camera in which each of the pixels (or array of them) corresponds to a photodetector. Thus, simultaneous measurements can be taken on the entire sample.

A first concept test of the present invention is described below and refers to FIGS. 4A, 4B, 4C and 4D. These figures show the spectral measurement of microcantilevers of the type used in microelectronic applications. This concept test was carried out in reflection in bright field mode, in other words, using a configuration similar to that in FIG. 1.

As a concept test in bright field mode, a spectral analysis was carried out on the surface of the commercially available silicon microcantilevers (300) (CLA-500-010-08, Concentris, GmbH, Switzerland); FIG. 4 shows images obtained from a scanning electron microscope and the main geometric characteristics of said microcantilevers are shown. The entire array is made up of eight microcantilevers connected to the chip (400) through a 6 µm thick pre-clamping region (301) (see FIG. 4A). Said microcantilevers (300) are 500 µm long, 100 µm wide and 1 µm thick. Measurements were made by using a microscope objective (10× LU Plan Fluor objective, Nikon, numerical aperture N.A. 0.3).

Figure 4A:
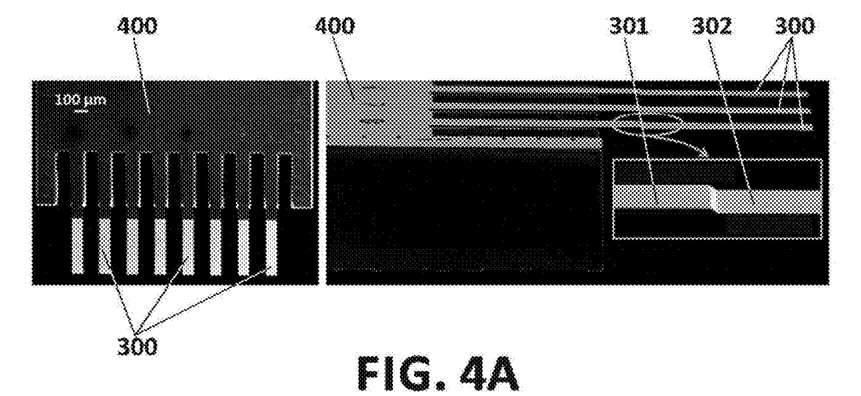
FIG. 4A shows, for a first concept test, a photograph obtained with a scanning electron microscope of an array of microcantilevers to be analyzed.

By using an objective with low magnification, we are able to have a detection area that is large enough to simultaneously measure four cantilevers. The microscope objective used guarantees a spatial resolution of approximately 1 µm. Optical measurements were made in the visible spectral range from 538 nm to 700 nm with steps of 1 nm and 1 ms of acquisition time for each image. Complete characterization of a sample takes less than 2 minutes.

All measurements were normalized with a silicon reference sample to eliminate spectral dependence of the light source, the CCD and all optical elements used. All information that is presented from now on for this concept test will take into account this normalization.

Figure 4B:
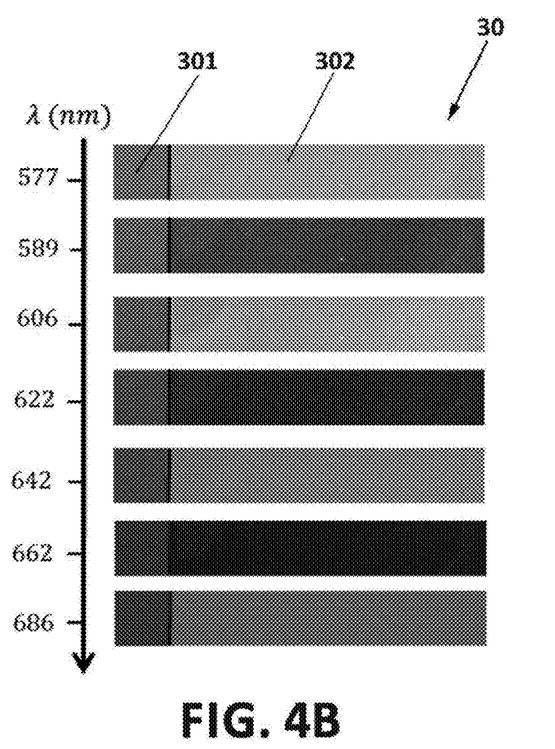
FIG. 4B shows the measurements of the light reflected by a microcantilever at different wavelengths.

In FIG. 4B, a first graph (30) shows measurements of the light reflected by a microcantilever at different wavelengths. Said measurements are taken simultaneously on all points on the surface, repeating this measurement for each of the wavelengths shown. The objects that are analyzed are: a first area (301) that corresponds to pre-clamping; and the microcantilever, which corresponds to a second area (302).

As shown in the first graph (30), measurements have been taken for wavelengths (λ) of 577 nm, 589 nm, 606 nm, 622 nm, 642 nm, 662 nm and 686 nm. Said measurements are taken sequentially (in other words, first for 577 nm, then for 589 nm, and so on).

The images in this first graph (30) show notable differences in the reflectivity of the microcantilever (in other words, in the second area (302)) depending on the wavelength, while in the first area (301) notable variations in reflectivity are not observed.

Figure 4C:
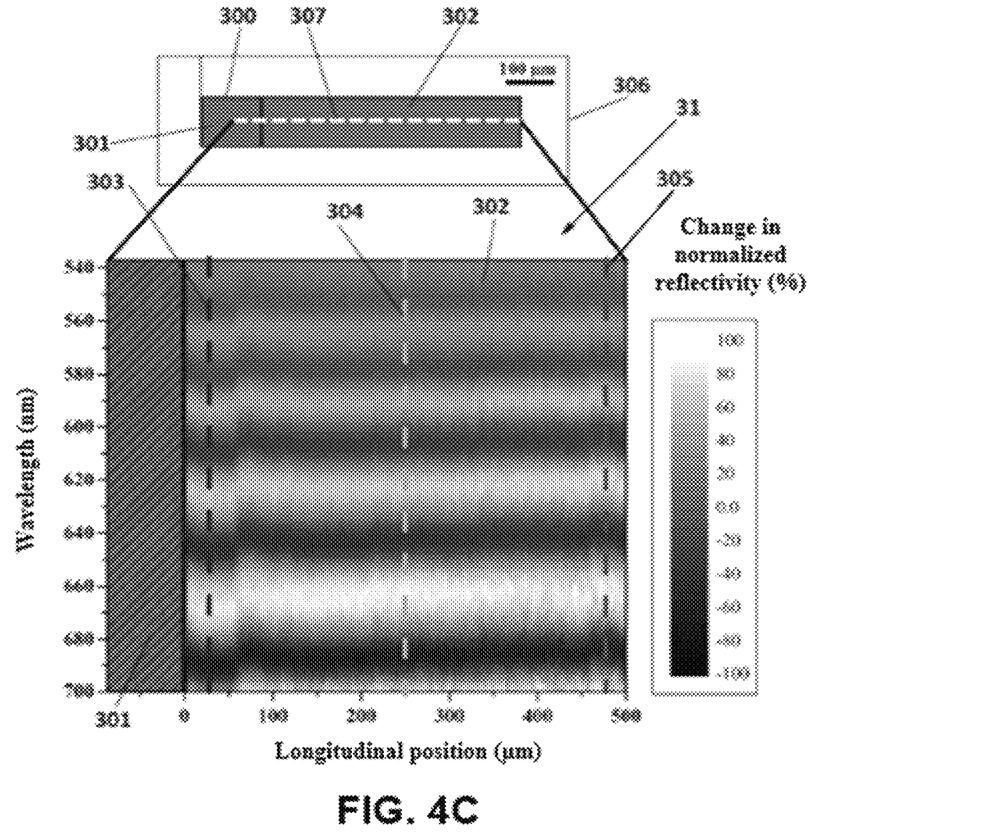
FIG. 4C shows a graph which shows the microcantilever for which the measurement was made, as well as the measurements of the percent change in normalized reflectivity of said microcantilever.

FIG. 4C shows an optical image (306) of a microcantilever (300) which has been measured, and under this microcantilever (300), a second graph (31) is shown with the measurements of the percentage change in normalized reflectivity obtained along the microcantilever (in other words, along the dashed line (307) of the optical image (306)) as a function of the wavelength (ordinate axis). In particular, three different points along said microcantilever will be analyzed: the base (303), an intermediate point (304) and the free end (305).

For each point on the microcantilever, reflectivity modulation as a function of wavelength can be observed. This modulation is due to the presence of multiple reflections inside the cantilever that can produce constructive interference (reflectivity maxima) or destructive interference (reflectivity minima) depending on the wavelength analyzed. In the case of the pre-clamping region, this type of modulation is not observed because the absorption of silicon does not allow multiple reflections inside a thicker structure (6 μm).

Figure 4D:
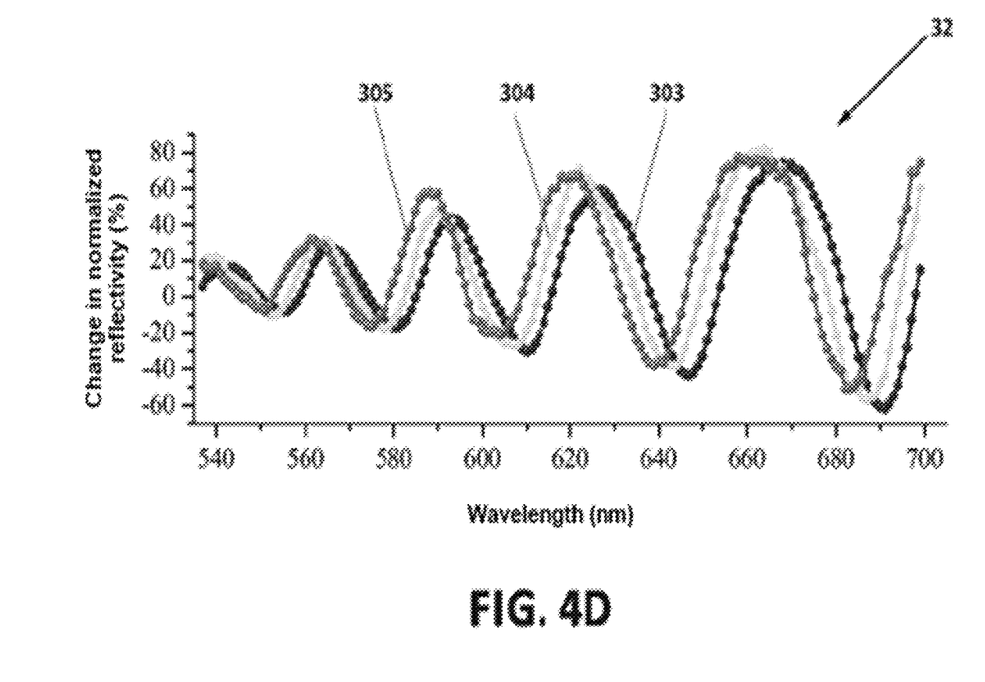
FIG. 4D shows a graph which shows the normalized reflectivity change as a function of the light emitter wavelength, obtained at three different positions along the microcantilever (near the clamped end of the microcantilever, at the middle and near the free end).

FIG. 4D shows a third graph (32) which shows how the reflectivity modulations shift between the base (303), the intermediate point (304) and the free end (305) due to variations in the thickness along the cantilever. In this concept test, the only parameter that modifies spectral shift is due to the change in the cantilever thickness, such that with this optical technique, the thickness of the structure studied can be easily calculated.

Figure 5:
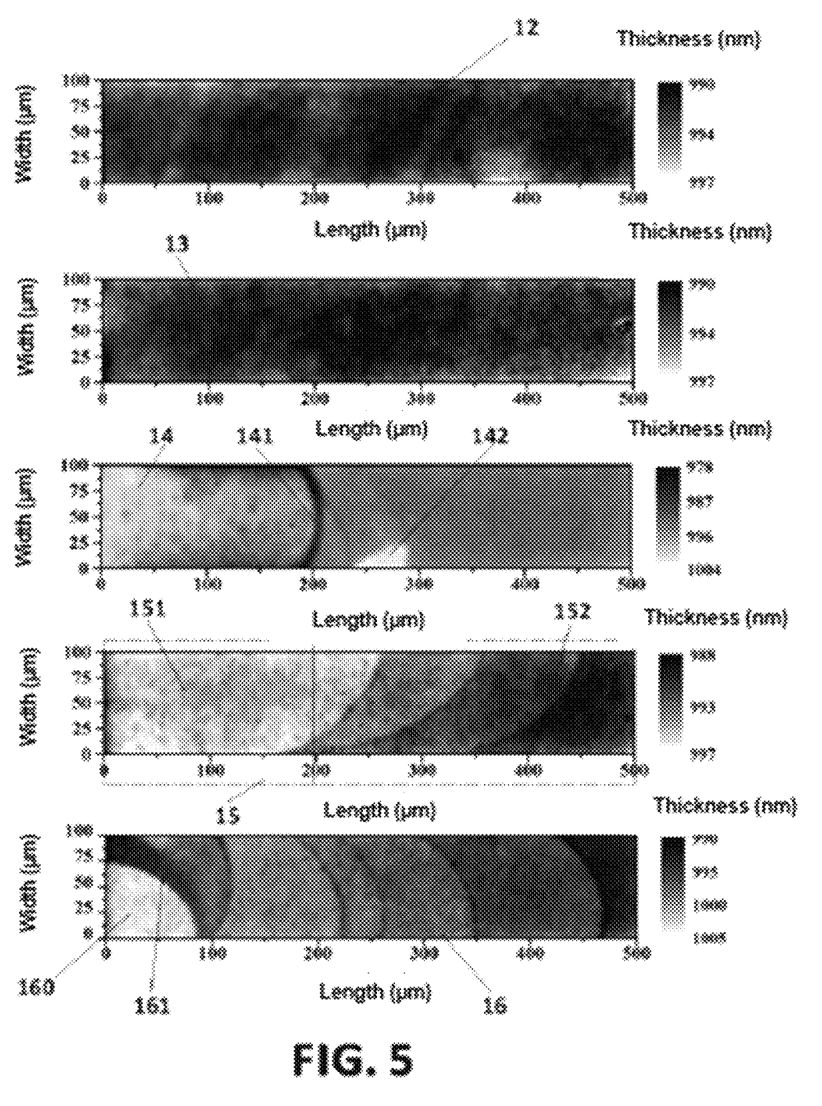
FIG. 5 shows a thickness map of several cantilevers using a spectrophotometric measurement in bright field mode with a device according to the present invention.

FIG. 5 shows a thickness map of 5 of the microcantilevers of FIG. 4A using a spectrophotometric measurement with a device according to the present invention, wherein the grayscale shown to the right of each figure represents the cantilever thickness expressed in nanometers. The thickness map was obtained through the analysis of the normalized reflectivity for each CCD pixel and the adjustment of said reflectivity to a theoretical model known in the state of the art. Each microcantilever is detected through approximately 50,000 pixels.

The thickness maps of FIG. 5 show, in a general way, significant thickness variations in several microcantilevers along the width thereof. Some of the microcantilevers, such as the first microcantilever (12) and the second microcantilever (13) present good thickness homogeneity, however, the third microcantilever (14), the fourth microcantilever (15) and the fifth microcantilever (16) show significant thickness variations that merit further analysis.

In particular, the third microcantilever (14) has a crack (141) with a thickness that is substantially thinner than the rest of its surface and a second step (142) that has a thickness significantly greater than the rest.

As for the fourth microcantilever (15), it has a first area (151) with a thickness substantially greater than that of a second area (152).

Lastly, the fifth microcantilever (16) has a first area (160) that is thicker near the clamping region and a second area (161) where its thickness is much less than the average thickness.

The second concept test consisted in the spectrophotometric study of 100 nm diameter gold plasmonic nanoparticles. In this case, the present invention is used for a dark-field reflectance spectroscopy measurement, as known in the state of the art, according to the experimental diagram shown in FIG. 1. To carry out dark-field spectroscopic measurements, the experimental system of the first concept test was modified, substituting the microscope objective with one from the dark-field (LU Plan Fluor 100×, Nikon, numerical aperture N.A. 0.9) and the beam splitter with one specific to this mode.

Figure 6:
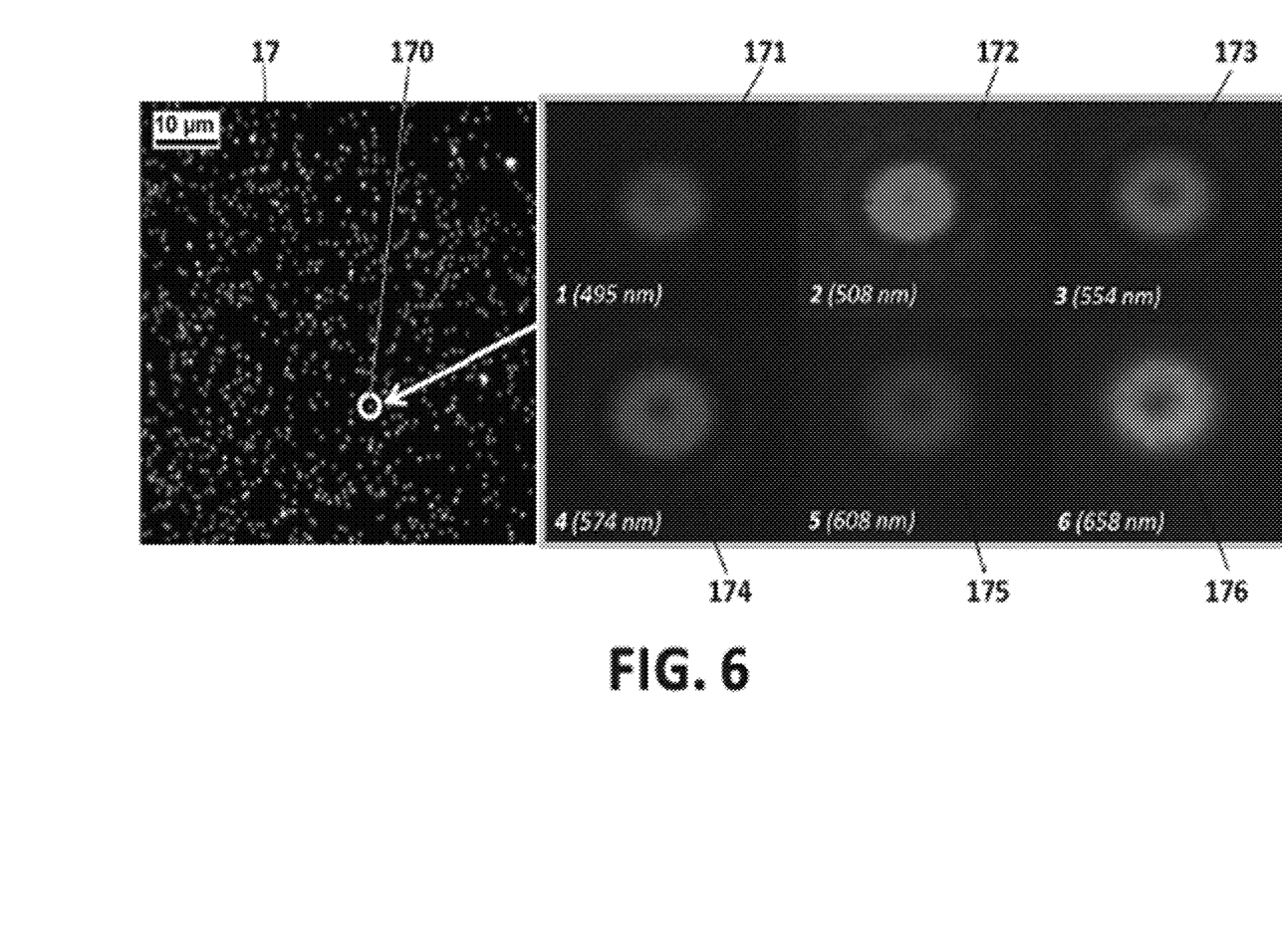
FIG. 6 shows microscope images obtained in dark field mode, in a second concept test, for plasmatic nanoparticles at different wavelengths.

As can be observed in FIG. 6, in this test, a silicon sample (17) with a series of gold nanoparticles deposited on it was measured. The high numerical aperture of the objective used (numerical aperture 0.9) guarantees, in this case, a spatial resolution of approximately 300 nm.

In the present invention, the entire sample (17) was measured without scanning the surface and only by sequentially illuminating the entire sample at various wavelengths for the different values of said wavelength. Measurements were taken in the visible spectral range from 480 nm to 680 nm with steps of 1 nm and an acquisition time of 30 ms for each image.

By way of illustration, FIG. 6 shows images of light scattered by a single nanoparticle (170) at some of the wavelengths of the visible spectral range, that is, at 495 nm (171), 508 nm (172), 554 nm (173), 574 nm (174), 608 nm (175) and 658 n (176).

In said measurements, it is observed that the behavior of the scattered light is different depending on the wavelength that is to be analyzed. The scattered light of said nanoparticle has been normalized according to a method that represents an important element of novelty compared to the previous experimental techniques.

Figure 7:
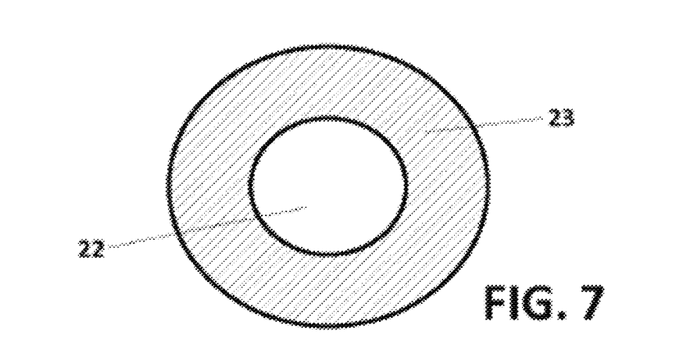
FIG. 7 shows an example of signal normalization obtained by means of spectrophotometry applicable to the concept test of FIG. 6.

FIG. 7 shows a schematic drawing of an embodiment of normalization of the signal obtained by means of spectrophotometry applicable to the concept test of FIG. 6.

Each light scattering object (22) has around it a darker region (23) that represents the scattered light that comes from the sample and that is very useful as a reference signal for the near light scattering object. In this way, signal normalization is carried out in a very specific way for each light scattering object, ensuring a notable increase in the signal-to-noise ratio measurement.

With this method of normalization, the signal to be measured is obtained through a single measurement, and likewise, the reference signal is obtained in the same experimental conditions (with the same intensity of the light source, the same focus and the same illumination intensity). Another added advantage of this aspect is that optical characterization of the sample is quicker since two successive measurements do not need to be taken, as is the case with the spectrometers of the prior art.

Figure 8:
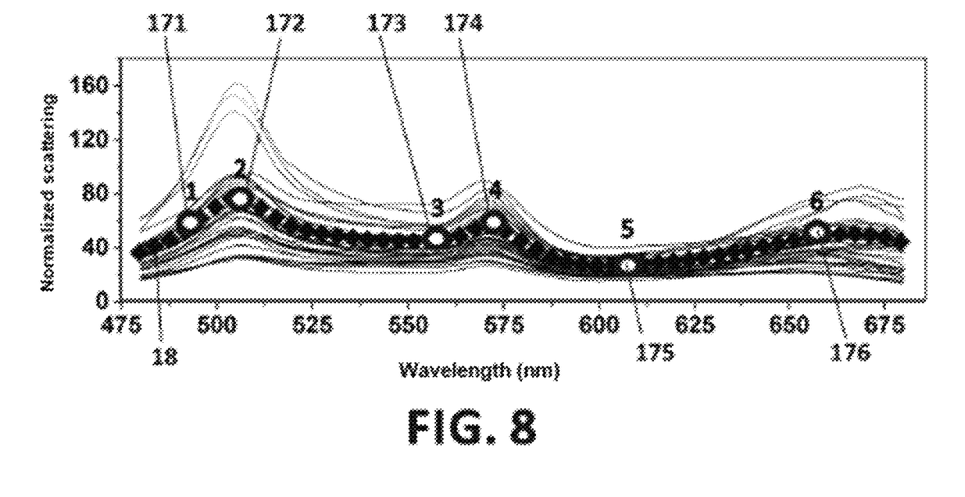
FIG. 8 shows the results obtained in the second concept test of spectrophotometry in dark field mode of plasmatic nanoparticles, using normalization of the type described, in reference to FIG. 7.

FIG. 8 shows the normalized spectra of the scattered light for various nanoparticles of FIG. 6.

The data was processed with a function written in Matlab®, which automatically recognizes all positions of the nanoparticles and carries out normalization of the scattered light for each of those nanoparticles.

Furthermore, it shows the normalized spectrum of the average scattering (18) of all nanoparticles of FIG. 6.

The invention claimed is:

1. A spectrophotometer for dark field measurements of the type that comprises a light beam emitter (1) directed on a sample (4) through a first optical path having an array of lenses, thereby sequentially illuminating the sample at various wavelengths, and an array of photodetectors (5) arranged on a second optical path defined as the path of the light beam after reflecting on the sample (4), characterized in that it comprises a processor for the light beam received by the photodetectors (5), said processor correlating each photodetector (5) to a spatial point on the sample (4), such that measurements are carried out sequentially across various wavelengths and in parallel along X-Y spatial coordinates, the spectrophotometer further comprising a dark field microscope objective (3) and a dark field beam splitter (20).

2. The spectrophotometer according to claim 1, characterized in that the emitter (1) comprises a light source (10) with a broad spectral band and a wavelength selector.

3. The spectrophotometer according to claim 2, characterized in that it comprises a modifier for the wavelength selected by the wavelength selector.

4. The spectrophotometer according to any of the claim 2 or 3, characterized in that the wavelength selector is a monochromator (11).

5. The spectrophotometer according to claim 1, characterized in that the emitter (1) comprises a series of light sources, each one of said light sources generating a light beam at a different wavelength.

6. The spectrophotometer according to claim 5, characterized in that it comprises a selector for the light source (10) that illuminates the sample (4).

7. The spectrophotometer according to claim 6, characterized in that the selector for the light source (10) that illuminates the sample comprise a sequential modifier for the source that illuminates the sample (4).

8. The spectrophotometer according to claim 1, characterized in that the array of photodetectors (5) is a CCD camera in which each one of the pixels of the series of pixels of said CCD camera is a photodetector.

9. The spectrophotometer according to claim 1, characterized in that the second path of the light beam comprises wireless transmitter of light.

\* \* \* \* \*